(12) United States Patent
Crawford et al.

(10) Patent No.: US 6,586,620 B1
(45) Date of Patent: Jul. 1, 2003

(54) PROCESS FOR THE PREPARATION OF ALKYL 3-OXO-2-PENTYL-1-CYCLOPENTENEACETATES

(75) Inventors: Khushrav Crawford, Sayreville, NJ (US); Valentin Rautenstrauch, Bernex (CH); Arnoldus Uijttewaal, Peron (FR)

(73) Assignee: Firmenich SA, Geneva (CH)

(*) Notice: Subject to any disclaimer, the term of this patent is extended or adjusted under 35 U.S.C. 154(b) by 0 days.

(21) Appl. No.: 10/140,795

(22) Filed: May 6, 2002

Related U.S. Application Data

(63) Continuation-in-part of application No. 09/703,880, filed on Nov. 2, 2000.
(60) Provisional application No. 60/163,563, filed on Nov. 5, 1999.

(51) Int. Cl.⁷ ................................................. C07C 69/74
(52) U.S. Cl. ........................ 560/126; 560/128; 549/546
(58) Field of Search ................................ 560/126, 128; 549/546

(56) References Cited

U.S. PATENT DOCUMENTS

| 5,302,745 A | * | 4/1994 | Winter | ........................ 560/126 |
| 5,874,600 A |   | 2/1999 | Rautenstrauch et al. | .... 536/136 |

FOREIGN PATENT DOCUMENTS

| EP | 0 810 903 | 12/1997 |

OTHER PUBLICATIONS

Chemical Abstracts, 73: 109363d (1970).
Chemical Abstracts, 75: 109953n (1971).
Chemical Abstracts, 76: 3462g (1972).
Chemical Abstracts, 99: 175481d (1983).
J. Org. Chem., vol. 39, No. 17, 2637 (1974).
J. Am. Chem. Soc., vol. 97, No. 21, 6144–6147 (1975).
Sisido et al., "Synthesis of Methyl Dihydrojasmonate", P. & E.O.R., 267–270 (Jul./Aug. 1969).
Van der Gen, "Corps olfactifs à l'odeur de jasmin", Parf. Cosm. Sav. France, vol. 2, No. 8, 356–370, (Aug.–Sep. 1972).

* cited by examiner

Primary Examiner—Alan L. Rotman
Assistant Examiner—Héctor M. Reyes
(74) Attorney, Agent, or Firm—Winston & Strawn

(57) ABSTRACT

The present invention discloses a process for the preparation of a compound according to formula

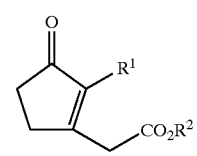

(I)

wherein $R^1$ is a $C_3$–$C_7$ alkyl group and $R^2$ is a $C_1$ to $C_4$, linear or branched, alkyl radical, more preferably a methyl group, characterized in that the process includes the isomerisation of an epoxide of formula

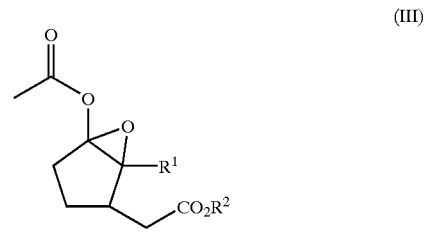

(III)

wherein $R^1$ and $R^2$ have the meaning given in formula (I), in the presence of an acidic isomerisation agent, a thermal treatment or a combination thereof. The process according to the invention allows the preparation of the cyclopentenyl compounds of formula (I) on an industrial scale. The compounds are important starting products for the production of appreciated perfuming ingredients in particular methyl dihydrojasmonates.

15 Claims, No Drawings

PROCESS FOR THE PREPARATION OF ALKYL 3-OXO-2-PENTYL-1-CYCLOPENTENEACETATES

CROSS-REFERENCE TO RELATED APPLICATIONS

This application is a continuation-in-part of application Ser. No. 09/703,880 filed Nov. 2, 2000, which claims the benefit of provisional application No. 60/163,563 filed Nov. 5, 1999.

FIELD OF THE INVENTION

The present invention relates to the field of organic synthesis. It relates, more particularly, to a process for the preparation of alkyl 3-oxo-2-pentyl-1-cylopentene-1-acetates of the general formula

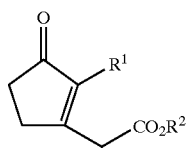

(I)

in which $R^1$ is a $C_3$–$C_7$ alkyl group and $R^2$ is a $C_1$ to $C_4$, linear or branched, alkyl radical, more preferably a methyl group. The present invention is also drawn to useful intermediate products in the synthesis of the above molecules of formula (I).

BACKGROUND OF THE INVENTION

The cyclopentene derivates (I) are important compounds for the preparation of the alkyl 3-oxo-2-alkyl-1-cyclopentaneacetates (II) which form a class of highly appreciated perfuming ingredients. There should be cited, in particular, the methyl 3-oxo-2-pentyl-1-cyclopentaneacetate, or methyl dihydrojasmonate, which is present in practically every perfume and which is, for example, on sale under the name Hedione® (origin: Firmenich SA, Geneva, Switzerland). There exist a large number of syntheses for the named methyl dihydrojasmonate and its homologues. A possible synthesis is the hydrogenation of the above cyclopentenyl derivatives (I), in order to transform the starting molecule into the compounds of formula (II), having a saturated $C_5$-ring.

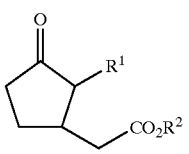

(II)

$R^1$ = $C_3$–$C_7$ alkyl group
$R^2$ = methyl, ethyl

From the above formula (II) it is clear that these compounds can exist in the form of several stereoisomers, due to the presence of 2 asymmetric carbon atoms. The hydrogenation processes described in the prior art give specific products, according to the conditions employed.

It is known that the catalytic hydrogenation of methyl 3-oxo-2-pentyl-1-cyclopentene-1-acetate, for example, in the presence of aluminum methoxide (see DE-OS 2 162 820) gives racemic cis-methyl-dihydrojasmonate the floral odor note of which is particularly appreciated by perfumers. Another hydrogenation process which makes use of chiral metal complexes is described in EP-B-810 903 (applicant: Firmenich SA). There is obtained the (IR)-cis-methyl dihydrojasmonate, which is the enantiomer showing the best olfactive qualities of all optical isomers.

There is hence a need for a process which can provide industrial amounts of the compounds of formula (1), in particular those in which $R^1$ is n-pentyl and $R^2$ is methyl, in order to have starting products for the synthesis of the above-mentioned qualities of the cyclopentyl compounds of formula (II).

The prior art reports a variety of syntheses of methyl 3-oxo-2-pentyl-1-cyclopenteneacetate. Among them, only one utilizes an acyclic derivative in its last step (see Jap. Pat. 58 118,536; Chem. Abstracts 1983, 99 175481 d), whereas the others have as key-intermediates cyclic compounds. According to the nature of these latters, the known processes can be classified in 5 different categories:

a. via a gamma-lactone by rearrangement in the presence of polyphosphoric acid (Dutch Pat. 69 18,228; Chem Abstracts 1971, 75, 109953 d);

b. via methyl dihydrojasmonate by bromination and dehydrobromination (Dutch Pat. 70 02,279; Chem. Abstracts 1972, 76, 3462 g) or by anodic oxidation of its enol-acetate (J. Am. Chem. Soc., 1975, 97, 6144);

c. via 2-pentyl-1,3-cyclopentanedione by reaction with dimethyl malonate (see e.g. DE-OS 2,008,833; Chem. Abstracts, 1970, 73, 109363 d);

d. via 2-pentyl-2-cyclopentene-1-one by radical addition of methyl dihydroxyacetate followed by dehydration (Parf. Cosm. Sav. France 1972, 2(8), 356); by reaction with methyl diazoacetate (Perf. Essent. Oil Rec. 1969, 267; JP 70 00862), or by addition of methyl bromoacetate (J. Org. Chem. 1974, 39, 2637) or of methyl lithioacetate followed by oxidation with chromic acid;

e. via isomerisation of certain epoxy-esters, namely alkyl 2,3-epoxy-2-pentyl-1-cyclopentylidene acetates, in the presence of an acidic isomerisation agent like mineral or organic protic acids or Lewis type acids (U.S. Pat. No. 5,302,745).

All those cited processes, however, do not allow an economic production of the desired cyclopentenyl derivatives of formula (I) on an industrial scale. The problem underlying the present invention was the finding of a process which does not show the disadvantages of those known in the prior art.

SUMMARY OF THE INVENTION

This problem is solved by a process for the preparation of a compound according to formula

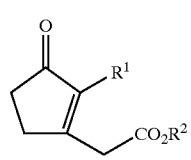

(I)

wherein $R^1$ is a $C_3$–$C_7$ alkyl group and $R^2$ is a methyl or ethyl group, characterized in that said process comprises the isomerisation of an epoxide of formula (III)

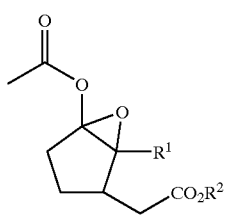

wherein R¹ and R² have the meaning given in formula (I), in the presence of an isomerisation agent, such as a Lewis or protic acid, a thermal treatment or a combination thereof.

This process is an important feature of the present invention.

DETAILED DESCRIPTION OF THE PREFERRED EMBODIMENTS

Typical isomerisation agents which can be used in the context of the present invention are known to a person skilled in the art and include mineral acids, organic protic acids and Lewis type acids. Specific examples of those acids are hydrochloric acid, sulfuric acid, phosphoric acid, p-toluenesulfonic acid, methanesulfonic acid, $BF_3$, $SnCl_4$, $TiCl_4$ and acidic ion exchange resins.

Additionally, a thermal treatment can be used as an isomerization agent. Preferably, a prolonged thermal treatment conducted at a temperature of between 140 and 220° C. for a time of between 1 and 10 hours is suitable. The thermal treatment can be used along with the acidic isomerization agent for optimum results.

The reaction takes place in the usual solvents. There can be cited here, as non-limiting examples, alcohols (e.g. methanol, ethanol and isopropanol), aromatic solvents (e.g. toluene and xylene), and ethers (e.g. diethyl ether).

Advantageous results could be obtained when methanol was used as solvent. Preferred acids include methanesulfonic acid, phosphoric acid and sulfuric acid. As methyl dihydrojasmonates are the preferred perfuming ingredients which can be prepared according to the process of the present invention, R¹ preferably is a n-pentyl group and R² is a methyl group.

The epoxides according to formula (III) can be prepared by the epoxidation of an enol acetate according to the formula (IV) below, in which R¹ and R² have the meaning given above for formula (I), with an epoxidising agent.

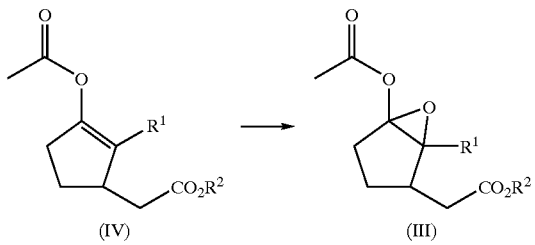

(IV)        (III)

For the epoxidation reaction, the usual reagents can be used. Non-limiting examples include peracids such as peracetic, performic and perpropionic acid, perbenzoic acid, m-chloroperbenzoic acid and MMPP (magnesium mono perphthalic acid). Hydroperoxides such as t-butylhydroperoxide and hydrogen peroxide can also be used.

It is preferred to use peracetic acid, most preferably peracetic acid in acetic acid.

The epoxides of formula (III) are novel compounds and form an object of the present invention, as well as the above-described process which leads to their formation.

In what concerns the enol acetates of formula (IV), these are known compounds. They can be obtained according to the method as described in J. Am. Chem. Soc. 97, p. 6144–6147 (1975).

It was observed that, depending on the conditions which were chosen when the epoxides of formula (III) are prepared or purified, two other products could be isolated, resulting also from a rearrangement reaction. These compounds can also be formed when the epoxides are submitted to the rearrangement reaction as described above.

One of these products is the cyclic ketone of formula (V)

(V)

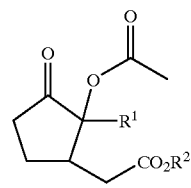

in which R¹ is a $C_3$–$C_7$ alkyl group and R² is a methyl or ethyl group. The ketones (V) are, for example, formed when the epoxides of formula (III) are submitted to a thermal treatment. Often, even at room temperature a certain degree of conversion occurs, whereas a complete conversion is often observed, for example, when the ketones are distilled. It has to be noted here that the synthesis of the cyclopentenyl compounds according to formula (I) is not hampered by the fact that the compounds (V) may be present. These compounds form the desired cyclopentenyl compound (I) under practically the same reaction conditions as do the epoxides, i.e. in presence of an appropriate acidic agent or by prolonged thermal treatment, or a combination thereof.

The other product which is formed from the epoxides (II), during their preparation or the rearrangement reaction being the object of the present invention, is the lactone (VI)

(VI)

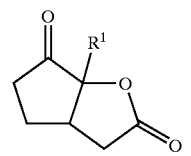

with R¹ being a $C_3$–$C_7$ alkyl group.

As mentioned above, the said lactone (VI) is formed under various conditions. For example, we could often observe its formation when the epoxidation reaction of the enol acetates (IV) was carried out without adding a base. In any case, the lactone (VI) can also be transformed into the cyclopentenyl compounds of formula (I), under reaction conditions which are similar to those required for the rearrangement of the epoxide (III).

EXAMPLES

The invention is illustrated by the following examples in which the temperatures are indicated in degrees Celsius and the abbreviations have the usual meaning in the art. The NMR data (chemical shift δ) are given in ppm with respect to TMS as internal standard.

Example 1

Preparation of Methyl 3-Acetoxy-2,3-epoxy-2-pentyl-1-cyclopentaneacetate

A four-necked, 3 l round-bottomed flask fitted with a mechanical stirrer, a thermometer, a reflux condenser and an addition funnel was charged with 646.0 g (2.41 mol) of methyl 3-acetoxy-2-pentyl-2-cyclopentene-1-acetate, 553 g of toluene and 22.0 g (0.2 mol) of sodium carbonate. Under vigorous stirring, there were then added 510.0 g (2.41 mol) of a 40% solution of peracetic acid in acetic acid, over 6 h at room temperature. When the addition was completed, stirring was continued for 30 min, before another 29 g (0.16 mol) of 40% peracetic acid in acetic acid were added, over 30 min at room temperature. Stirring was again continued for 2 h at room temperature, 200 g of water were added and the resulting phases separated. The organic phase was washed 4 times with 200 g of water. The solvent was then evaporated under reduced pressure to obtain 714.9 g of epoxide which can be used as such in the next reaction.

$^1$H-NMR: 0.90 (br t, J=6.7 Hz, Me); 1.02–1.17 (m, 1H); 1.20–1.56 (series of overlapping m, 7H); 1.78–2.68 (series of overlapping m, 7H); 2.11 (s, MeCO$_2$); 3.68 (s, MeO). $^{13}$C-NMR: 13.9 (Me), 21.0 (MeCO$_2$), 22.4, 24.5, 26.3, 27.2, 28.2, 31.9, 34.4 (CH$_2$), 36.0 (CH), 51.7 (MeO), 71.2, 91.8 (C), 169.5, 172.9 (CO$_2$). MS (electrospray ionization): (M+H)$^+$=285.

Under other MS conditions, the compound gives the same spectrum as methyl 2-acetoxy-3-oxo-2-pentyl-1-cyclopentaneacetate (see below).

The epoxide prepared as described above can be transformed into methyl 2-acetoxy-3-oxo-2-pentyl-1-cyclopentaneacetate by distillation on a Vigreux-type column, under atmospheric pressure. Like that, a pure compound is obtained which shows the following data:

$^1$H-NMR: 0.88 (br t, J=6.7 Hz, Me); 1.17–1.56 (series of overlapping m, 8H); 1.59–1.74 (m, 1H); 2.04 (s, MeCO$_2$); 2.14–2.69 (series of overlapping m, 5H); 3.29–3.42 (m, 1H); 3.70 (s, MeO). $^{13}$C-NMR: 14.0 (Me), 20.9 (MeCO$_2$), 21.7, 22.4, 24.2, 29.9, 32.3, 34.3, 34.6 (CH$_2$), 38.7 (CH), 51.7 (MeO), 85.2 (C), 169.7, 172.2 (CO$_2$), 211.9 (CO). MS: 209 (18), 151 (20), 130 (48), 111 (23), 99 (34), 98 (46), 71 (24), 55 (46), 43 (100).

Example 2

Preparation of 1-Pentyl-2-oxabicyclo[3.3.0]octan-3,8-dione

A 2000 ml three-necked round-bottom flask, equipped with a magnetic stirrer, nitrogen device, thermometer, dropping funnel and a reflux condenser was charged with 591.0 g of crude methyl 3-acetoxy-2-pentyl-2-cyclopentene-1-acetate and 70 g of toluene. At 26° C. 386.9 g (2.04 mol) 40% peracetic acid were added dropwise over a 5.3 h period. Stirring was continued for 2 h. 22.0 g (0.12 mol) of 40% peracetic acid were added over 30 min, and stirring was continued for another 2 h. 350 g of water were added and the water-layer (590.4 g) was separated. Three more washes were made with each 350 ml of water. The organic phase (1273.9 g) was evaporated to give 437.8 g of crude product which was vacuum distilled (0.4 hPa) to furnish 2 fractions, of which the first one (Bp=90–144° C.) was 172.55 g, containing 26.5% of product and the second one was 187.6 g, containing 95% of lactone. $^1$H-NMR: 0.88 (br t, J=6.7 Hz, Me); 1.15–1.45 (m, 6H); 1.67–1.87 (m, 3H); 2.14–2.63 of overlapping m, 4H); 2.84–2.97 (m, 2H). $^{13}$C-NMR: 13.9 (Me), 22.4, 22.6, 25.0, 31.9, 33.0, 35.7, 35.8 (CH$_2$), 38.6 (CH), 89.0 (C), 175.0 (CO$_2$), 210.9 (CO). MS: M$^+$=210 (5): 154 (16), 139 (22), 112 (25), 111 (73), 99 (79), 98 (100), 83 (26), 71 (26), 55 (73), 43 (28).

Example 3

Preparation of Methyl 3-oxo-2-Pentyl-1-cyclopenteneacetate

A 1000 ml three-necked round-bottom flask, equipped with a magnetic stirrer, nitrogen device, thermometer, dropping funnel and a reflux condenser was charged with 1400 g of methanol and 14.0 g of methanesulfonic acid. The reaction mixture was heated to reflux (65° C.) and 763.0 g (2.68 mol) of crude epoxide obtained according to Example 1 were added dropwise over 6 h. Reflux was continued for 2 h after the addition. Methanol was evaporated at reduced pressure and the crude product was dissolved in 140 g of cyclohexane and washed with 12.4 g of sodium acetate in 140 g of water. After solvent evaporation, the crude product (616.8 g) was distilled under reduced pressure (0.1 hPa). The product is obtained in a yield of 73%. In order to obtain a material with a better purity, the product may have to be redistilled.

When the above procedure was repeated, replacing the epoxide by the lactone obtained according to Example 2, the same product (methyl 3-oxo-2-pentyl-1-cyclopenteneacetate) was obtained. However, the yields were lower and the product obtained showed a lower purity.

What is claimed is:

1. A process for the preparation of a compound according to formula

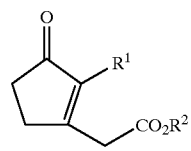

(I)

wherein R$^1$ is a C$_3$–C$_7$ alkyl group and R$^2$ is a C$_1$ to C$_4$, linear or branched, alkyl radical, which process comprises the isomerisation of an epoxide of formula

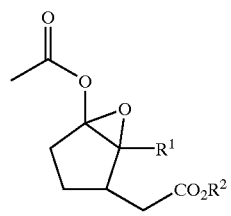

(III)

wherein R$^1$ and R$^2$ have the meaning given in formula (I), by means of an isomerisation agent.

2. A process according to claim 1, characterized in that said isomerisation agent is selected from the group consisting of hydrochloric acid, sulfuric acid, phosphoric acid, p-toluenesulfonic acid, methanesulfonic acid, BF$_3$, SnCl$_4$, TiCl$_4$ and acidic ion exchange resins.

3. A process of claim 2 wherein the isomerisation agent is methanesulfonic acid, phosphoric acid or sulfuric acid.

4. A process according to claim 1, said isomerisation is carried out in an alcohol.

5. A process of claim 4 wherein the alcohol is methanol.

6. A process according to claim 4, wherein said isomerisation proceeds via a cyclic ketone of formula

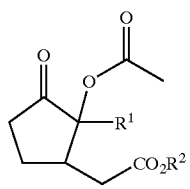
(V)

or a lactone of formula

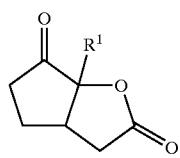
(VI)

wherein $R^1$ and $R^2$ have the meaning given in claim 1, said ketone (V) or said lactone (VI) being formed from said epoxide (III).

7. A process according to claim 6, wherein $R^1$ is a n-pentyl group and $R^2$ is a methyl group.

8. A process according to claim 1, characterized in that said isomerisation agent is a thermal treatment.

9. A process according to claim 8, characterized in that said thermal treatment is conducted at a temperature of between 140 and 220° C. for a time of between 1 and 10 hours.

10. A process according to claim 8, wherein said isomerisation proceeds via the formation of a cyclic ketone of formula (V), said cyclic ketone (V) being formed from said epoxide (III).

11. A process according to claim 10, wherein $R^1$ is a n-pentyl group and $R^2$ is a methyl group.

12. A compound of formula

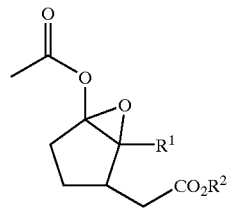
(III)

wherein $R^1$ is a $C_3$–$C_7$ alkyl group and $R^2$ is a methyl or ethyl group.

13. A compound according to claim 12, characterized in that $R^1$ is a n-pentyl group and $R^2$ is a methyl group.

14. A compound of formula

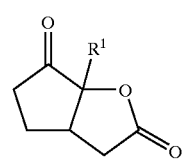
(VI)

wherein $R^1$ is a $C_3$–$C_7$ alkyl group.

15. A compound according to claim 14, characterized in that $R^1$ is a n-pentyl group.

* * * * *